United States Patent [19]

Masaki et al.

[11] 4,378,438
[45] Mar. 29, 1983

[54] TRAY FOR IDENTIFYING MICROORGANISMS FOR USE IN A DIGITAL MOVING MAP DISPLAY

[75] Inventors: Toshikatsu Masaki, Niiza; Seiji Enomoto, Saitama; Michiya Kimura, Oyama, all of Japan

[73] Assignee: Eiken Chemical Co., Ltd., Tokyo, Japan

[21] Appl. No.: 316,327

[22] Filed: Oct. 29, 1981

Related U.S. Application Data

[63] Continuation of Ser. No. 171,817, Jul. 24, 1980, abandoned.

[30] Foreign Application Priority Data

Nov. 6, 1979 [JP] Japan .................................. 54-153992

[51] Int. Cl.³ ............................................... C12M 1/20
[52] U.S. Cl. .................................... 435/301; 435/808; 422/57; 422/61
[58] Field of Search .............................. 435/299–301, 435/293, 294, 808; 422/57, 62, 61

[56] References Cited

U.S. PATENT DOCUMENTS 4,076,592 2/1978 Bradley ................................ 435/301
4,239,853 12/1980 Bradley ............................... 435/301

Primary Examiner—Benoit Castel
Attorney, Agent, or Firm—Parkhurst & Oliff

[57] ABSTRACT

A tray for identifying isolated microorganisms consisting of a plastic or glass tray body and a transparent cover, the body surface of which has two kinds of hollows for bacterial suspensions. One is formed horizontally across the surface of the tray and the other is composed of number of small wells long and slender, put parallel and rectangular to previous hollow. Each of the small cells communicates over crest barrier to hollow put horizontally. With this tray, microorganisms can be exactly and easily identified.

3 Claims, 3 Drawing Figures

TRAY FOR IDENTIFYING MICROORGANISMS FOR USE IN A DIGITAL MOVING MAP DISPLAY

This is a continuation of application Ser. No. 171,817 filed July 24, 1980, now abandoned.

BACKGROUND OF THE INVENTION

This invention relates to identifying microorganisms and, more particularly, to a tray containing trace amounts of reagents for identifying microorganisms.

In order to generally identify microorganisms, it is necessary to perform the steps of isolating the microorganisms via isolation media, inoculating them in more than twenty kinds of confirmation media with purely isolated bacteria, culturing them in an incubator at 37° C. for 24 to 48 hours, and then detecting the biochemical properties of the bacteria to be tested. Accordingly, an aseptic operation is necessary to prepare the media with complicated operation for identifying the microorganisms thus cultured.

SUMMARY OF THE INVENTION

The inventors of this invention have developed a tray for identifying microorganisms as a result of a variety of studies for readily identifying bacterias to be tested.

It is therefore a primary object of this invention to provide a tray for identifying microorganisms which can eliminate the aforementioned disadvantages and drawbacks of the conventional microorganism identification and can exactly identify the microorganisms with the biochemical properties of the microorganisms without erroneous operation in short time.

It is another object of this invention to provide a tray for identifying microorganisms which can be inoculated with bacterial suspension simply by one step.

It is still another object of this invention to provide a tray for identifying microorganisms on which bacterial suspension can smoothly be distributed.

It is still another object of this invention to provide a tray for identifying microorganisms which can uniformly branch bacterial suspension in each cell.

The tray of this invention is formed by plastic or consists of a plastic or glass tray body and a transparent cover so that a cell for bacterial suspension is formed longitudinally of the tray body and a number of small cells (such as, for example, 20 cells) perpendicularly to the cell for bacterial suspension. Each of the culture cells communicates over a crest barrier with the cell for bacterial suspension. It is preferable to provide a plurality of partition barriers extended toward the cell for bacterial suspension for dividing the approach portion of the crest barrier passage in order to uniformly introduce the bacterial suspension into the respective small cells in the approach portion.

In each small cell, dried or tablet type reagents are placed corresponding to the items of the biochemical characteristics to be investigated in such an amount as needed per test. After pouring bacterial suspension into small cell through cell for bacterial suspension, color of the reagent changes due to biochemical characteristics of the microorganisms. It is sometimes necessary to further add several types of reagents to the small cell according to type of biochemical reaction.

Any biochemical properties capable of identifying the microorganisms may be widely available in this invention. Such biochemical properties are, for example, indole production ability, VP reaction, urea resolving power, citrate availability, malonate utility, ONPG, arginine decarboxyl ability, ornithine decarboxyl ability, lysine decarbocyl ability, saccharose degradation ability, adonitol degradation ability, arabinose degradation ability, sorbitol degradation ability, rhamnose degradation ability, inositol degradation ability, dulcitol degradation ability, mannitol degradation ability, xylose degradation ability, etc.

According to this invention, purely isolated bacterias are suspended in physiological saline or the like, pouring specified quantity of bacterial suspension into the cell for bacterial suspension, retaining the tray horizontally to level the bacterial suspension unformly in the cell for bacterial suspension, then inclining the entire tray so that the bacterial suspension moves from the cell for bacterial suspension to small cells over the crest barrier passages, respectively. Then a transparent cover is put on the tray to incubate so as to develop reactions according to the type of the biochemical properties. Correct identification can be achieved by observing biochemical reactions accompanying corresponding color change occured in small cells.

BRIEF DESCRIPTION OF THE DRAWINGS

These and other objects of the invention will be seen by reference to the description, taken in connection with the accompanying drawings, in which.

DESCRIPTION OF THE PREFERRED EMBODIMENTS

Figure 1:
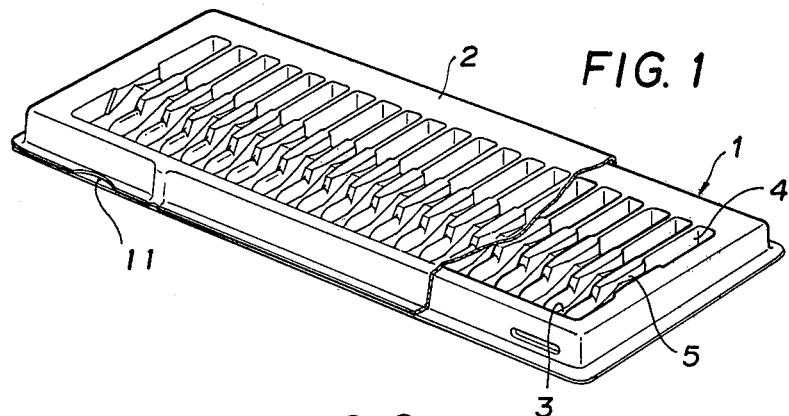
FIG. 1 is a perspective view of one preferred embodiment of the tray partly broken at the cover constructed according to this invention.
Figure 2:
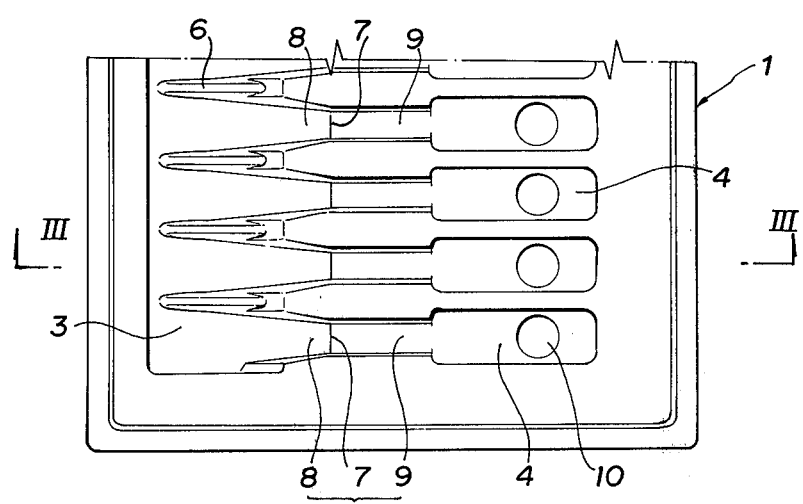
FIG. 2 is a partially enlarged plan view of the tray body shown in FIG. 1.

Referring now to the drawings, and particularly to FIG. 1 showing one preferred embodiment of the tray with its cover partically broken and to FIG. 2 showing the partial expansion of the tray body shown in FIG. 1, wherein like reference numerals designate the same parts in the following views, the tray of this invention consists of a rectangular thin box-shaped tray body 1 and a cover 2. A cell for bacterial suspension 3 is formed longitudinally of the tray body 1 at one side thereof and a number of small cells 4 are formed perpendicularly to the cell for bacterial suspension 3. Each of the small cells 4 communicates through a crest barrier passage 5 with the cell for bacterial suspension 3. The tray body 1 is formed by plastic such as vinyl chloride, polypropylene or the like and is formed by vacuum or compression molding, the plastic sheet having less than 0.5 mm thick or the like. It should be noted that in case that the plastic sheet is thicker than 0.5 mm, the respective cells and the passages are not formed in sharp manner to thus cause the bacterial suspension to improperly flow therethrough.

There are provided a plurality of partition barriers 6 extended toward the cell for bacterial suspension in the cell 3 for preferably introducing the bacterial suspension through the crest barrier passage 5 into the respective small cells 4.

Figure 3:
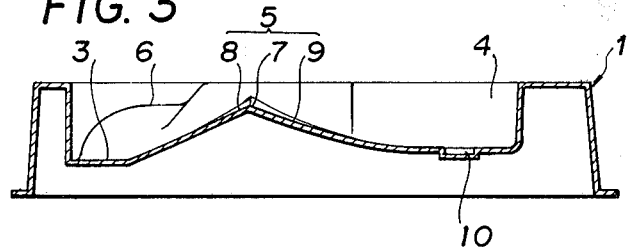
FIG. 3 is a sectional view of the tray body taken along the line III—III in FIG. 2.

As shown in FIGS. 2 and 3, each of the crest barrier passage 5 is formed narrower than the width of the small cell 4 and consists of an approach portion or passage 8 rising at a predetermined constant gradient from the cell for bacterial suspension 3, a crest 7 formed at the top of the raising approach portion 8, and a U-shaped downward portion or passage 9 downwardly curved longitudinally of the passage 5 at its bottom from the crest 7 to arrive coincidentally at the bottom of the small cell 4 at the lowermost end thereof in U shape for preventing counterflowing of the bacterial suspension as can be seen from FIG. 3.

It is noted that although the passage 9 is bent from directly under the crest 7 in U shape at its bottom as shown in FIG. 3, it may also be formed with an oblique groove with a rectangular bottom toward the small cell 4 from the crest 7 and curved from the slightly lower portion than the crest 7 so that the bottom of the curved portion is formed in U shape in cross section.

It is also noted that the small cell 4 exemplified above is remarkably shallower than the cell for bacterial suspension. However, when the small cell 4 is formed as deep as the cell for bacterial suspension 3, the bacterial suspension may be smoothly distributed into the small cells 4 to allow operation even when the tray body 1 is stood upward. It is also noted that though there is a shallow recess 10 formed substantially at the center of each of the small cells 4 for filling reagent, it is not always necessary. As the reagent, a sterilized reagent for conducting a biochemical test may also be used in dry state, and is filled in the small cells to thereby gas sterilize the entire tray. When the reagent is dried, dry hot blast is preferable. In case of powder reagent, PVP (polyvinyl pyrrolidone) is mixed in suitable amount with the reagents to thereby prevent them from peeling off or scattering in its drying process.

The cover 2 coating the tray body 1 is transparent, and is formed with a plurality of cutouts 11 conveniently for gripping the cover when standing and operating the tray body 1. Reagent numbers or symbols may also be marked on or side of the respective small cells 4 of the tray body 1 or the reagent number may be marked at the side of the tray body 1, and the symbol may be marked at the cover 2 at the position corresponding thereto. At the time of using this tray thus constructed, reagents for biochemical tests are placed in small cells before-hand. Then, pure isolate to be tested, suspended in appropriate concentration in saline, is poured into a cell for bacterial suspension 3 in specified amount, retaining the tray body 1 horizontally to uniformly level the bacterial suspension in the cell for bacterial suspension 3, then the entire tray body 1 is inclined so that the bacterial suspension cell is raised, where the cell for suspension becomes high to thereby introduce the bacterial suspension into the respective small cells 4 over the crest barrier passages 5.

It is noted that the cover 2 may be placed on the tray body 1 after pouring the bacterial suspension or may be put on the tray body 1 after inoculating it. Then, the bacteria inoculated is cultured by the conventional process to thereby react according to the type of the biochemical characteristics and the color change is to be observed. Thus, this tray body can exactly identify the biochemical properties of the bacterias without erroneous operation in short time.

When this tray body 1 is used, hydrophilic surfactant is coated on or printed on the cell for bacterial suspension 3, and hydrophobic surfactant active agent or silicon oil or the like is coated or printed on the crest barrier passage to thereby uniformly distribute the bacterial suspension into the small cells, and when the tray body 1 is inclined, it can prevent suspension from reversely flowing from the small cells 4 into the cell for bacterial suspension 3. When a surfactant reactive reagent solution dissolved in alchohol therein is poured and alcohol is volatilized to leave the surfactant, the distribution of the bacterial suspension into the small cells may further be improved. When the surfactant is dissolved in the bacterial suspension, and hydrophilic surfactant is coated on the crest barrier passage, best result can be obtained.

In case of anaerobic bacterial suspension, the small cells 4 are sealed on its upper surface by a transparent film and the tray body 1 is stood vertically to thereby place liquid paraffin on the bacterial suspension solution to culture the bacteria in ana robic state while retaining vertical state as it is so as to thus investigate it.

The example of the tray body having ten small cells will now be compared in respect of the quantity of distributed bacterial suspension (the quantity of inoculated bacterias) as below.

In the following Table, reference character A designates the date in the small cell and the cells for bacterial suspension coated by Triton X405 (made by Rohn & Haas company) on the crest barrier passage and the small cells coated with silicon oil on the barrier passage of the small cell side.

| Small cell number | A saline (ml) | | B saline (ml) | | A saline with surfactant (ml) | | C saline with surfactant (ml) | |
|---|---|---|---|---|---|---|---|---|
| | | Bacteria suspension | | | | | | |
| 1 | − | 0 | + | 0.18 | ± | 0.16 | + | 0.19 |
| 2 | − | 0 | ± | 0.17 | + | 0.18 | + | 0.19 |
| 3 | − | 0 | + | 0.20 | + | 0.20 | + | 0.19 |
| 4 | − | 0.10 | + | 0.19 | + | 0.22 | + | 0.20 |
| 5 | + | 0.50 | + | 0.21 | + | 0.19 | + | 0.20 |
| 6 | + | 0.50 | + | 0.20 | + | 0.21 | + | 0.20 |
| 7 | + | 0.40 | + | 0.20 | ± | 0.17 | + | 0.20 |
| 8 | − | 0.10 | + | 0.19 | + | 0.21 | + | 0.20 |
| 9 | − | 0 | + | 0.18 | + | 0.18 | + | 0.21 |
| 10 | − | 0 | + | 0.21 | + | 0.20 | + | 0.19 |
| Distributed quantity | | 2.00 | | 2.00 | | 2.00 | | 2.00 |
| Recovered quantity | | 1.60 | | 1.93 | | 1.92 | | 1.97 |

(NOTE: +; positive, −; negative)

As may obviously be understood from the Table, in comparing the tray body made of plastic with the tray body coated with surfactant and silicone oil, the inoculated quantity of the bacterial suspension was irregular by the tray body not treated to thereby cause the cultural ability of the tray body to be effected by the irregular quantity. On the other hand, the quantity of the inoculated bacterial suspension of physiological saline solution containing surfactant or by the tray body coated with the surfactant and silicone oil was stable exhibiting superior culture result of the bacteria. In case of the above C, when the downward passage of the crest barrier passage is formed in H shape bottom, it may omit the coating of silicone oil thereon so as to obtain the same result.

It should be understood from the foregoing description that since the tray body of this invention is used to perform the steps of pouring predetermined quantity of bacterial suspension in the cell for bacterial suspension thereof, retaining it horizontally, and then inclining one end thereof to thereby inoculate in the respective small cells over the crest barrier passage simply by one operation, the bacteria is cultured with the cover coating the tray body to thereby effect the discrimination of the biochemical properties of the bacteria or microorganisms responsive to the type of the biochemical characteristics shown in small cell in short time.

What is claimed is:

1. A tray for identifying microorganisms comprising:
a tray body and a cover;
a plurality of substantially parallel partition walls formed at substantially equal intervals in said tray body;
a plurality of small cells separated by said partition walls, each comprising relatively wide end sections and a narrow intermediate section;
a plurality of crest barriers, one formed substantially across each of said small cells and located in said intermediate section, and dividing said small cells into first and second portions, said crest barriers being substantially co-linear, said second portions having a bottom section which comprises a reagent holding recess;
a cell for bacterial suspension formed by the first portions of said small cells, said partition walls decreasing in height and width in the direction from the crest barrier toward the cell for bacterial suspension and extending only partly across said cell for bacterial suspension;
a plurality of similarly-dimensioned cells for culturing bacteria, each formed by one second portion of said small cells, said cells for culturing bacteria being of substantially rectangular configuration, the width of said cells for culturing bacteria being greater than the width of said narrow intermediate sections, the intersection of each of said intermediate sections with each of said cells for culturing bacteria being abruptly defined by said partition walls, said bacterial suspension cell and each of said cells for culturing bacteria being in communication over the crest barriers; and
a groove formed in each of said cells for culturing bacteria, wherein one end of said partition walls is formed as a partition barrier raised from the interior of the cell for bacterial suspension, said crest barriers being lower than the top of said partition wall at the top and smoothly raised from both the cell for bacterial suspension and said cells for culturing bacteria, at least part of said partition walls in the vicinity of said crest barrier extending upwardly so as to be level with the top of said tray body, wherein hydrophilic surfactant is coated on the smoothly raised surface of the cell for bacterial suspension side of the crest barrier, and at least one member selected from the group consisting of hydrophobic surfactant and silicone oil is coated on the smoothly raised surface of the cell for culturing bacteria side of the crest barrier.

2. A tray as claimed in claim 1, wherein each of said first portions are formed so as to have a flat portion which rises substantially at a predetermined gradient to said crest barriers, and each of said second portions comprises a curved section connecting said bottomsection extending substantially from the portion of said bottom section nearest said crest barrier to said crest barrier, the perpendicular distance from said crest barriers to the far edge of said cells for culturing bacteria being greater than the perpendicular distance from said crest barriers to the far edge of said cell for bacterial suspension.

3. A tray as claimed in claim 2, wherein the vertical difference between said crest barrier and said cell for bacterial suspension being greater than that between said crest barrier and said cells for culturing bacteria.

* * * * *